United States Patent [19]

Boesten et al.

[11] Patent Number: 5,336,805

[45] Date of Patent: Aug. 9, 1994

[54] PROCESS FOR PREPARING AN α-AMINO ACID, THE CORRESPONDING ESTER AND AMIDE

[75] Inventors: Wilhelmus H. J. Boesten, Sittard; Nicolaas A. de Heij, Leende, both of Netherlands

[73] Assignee: DSM N.V., Heerlen, Netherlands

[21] Appl. No.: 928,317

[22] Filed: Aug. 12, 1992

[30] Foreign Application Priority Data

Aug. 13, 1991 [NL] Netherlands ............... 9101380

[51] Int. Cl.$^5$ .................................... C07C 229/00
[52] U.S. Cl. ........................... 562/444; 562/443; 562/507; 562/553; 562/575; 560/19; 560/38; 560/39; 560/40; 560/41; 564/134; 564/135; 564/136
[58] Field of Search ......... 562/444, 443, 507, 553, 562/575, 445, 446, 447, 449, 450; 560/19, 38, 39, 40, 41; 564/134, 135, 136

[56] References Cited

U.S. PATENT DOCUMENTS

| | | | |
|---|---|---|---|
| 3,073,821 | 1/1963 | Johl et al. | 562/444 |
| 4,175,206 | 11/1979 | Senuma et al. | 562/444 |
| 4,205,185 | 5/1980 | Elton et al. | 562/444 |
| 4,233,456 | 11/1980 | Schmand et al. | 562/401 |
| 4,281,180 | 7/1981 | Umezawa et al. | 562/444 |

FOREIGN PATENT DOCUMENTS

| | | | |
|---|---|---|---|
| 0046741 | 4/1979 | Japan | 562/444 |
| 0061191 | 5/1979 | Japan | 562/444 |
| 1371896 | 10/1974 | United Kingdom | 562/444 |
| 1576678 | 10/1980 | United Kingdom | 562/444 |

OTHER PUBLICATIONS

Cohen-adad, "Sulfamic Acids". ca90(20):154219y/DE 2827553. Jan. 4, 1979, abstract only.

*Primary Examiner*—José G. Dees
*Assistant Examiner*—Keith MacMillan
*Attorney, Agent, or Firm*—Cushman, Darby & Cushman

[57] ABSTRACT

Process for preparing an a-amino acid having the general formula (1) of $$R-\underset{\underset{NH_2}{|}}{CH}-\overset{O}{\underset{}{\overset{\|}{C}}}-OH \qquad (1)$$

where R represents an aryl group or a substituted aryl, cycloalkyl or alkyl group, in which process glyoxylic acid, or a precursor or derivative thereof, is contacted in the presence of sulphamic acid with an unsaturated compound chosen from the group of aromatics, cycloalkenes and alkenes. By applying the process higher efficiencies are obtained.

The acid obtained as reaction product can be esterified and amidated without prior isolation.

9 Claims, No Drawings

PROCESS FOR PREPARING AN α-AMINO ACID, THE CORRESPONDING ESTER AND AMIDE

The invention relates to a process for preparing an α-amino acid having the general formula (1) of

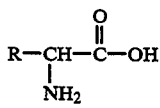

where R represents an aryl group or a substituted aryl, cycloalkyl or alkyl group, in which process glyoxylic acid having the formula (2) of

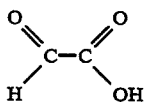

or a precursor or a derivative thereof is contacted with an aromatic compound, a cycloalkene and/or an alkene, in the presence of a N-containing compound.

From GB-A-1371896, for instance, a process is known in which, in addition to phenol and glyoxylic acid, ammonia is used as N-containing compound.

A disadvantage of the known process is that a low conversion efficiency is reached. For instance, in the preparation of p-hydroxyphenyl glycine the efficiency achieved is not higher than about 40% calculated on the amount of glyoxylic acid, while, moreover, in the processes described an excess of phenol and ammonia is used calculated on glyoxylic acid.

With the invention a process is provided by which higher efficiencies are realized.

This is achieved according to the invention by carrying out the reaction in the presence of sulphamic acid ($NH_2SO_3H$).

The fact is that, whereas according to the known processes only a relatively low yield of p-hydroxyphenyl glycine is obtained under basic conditions using ammonia or salts thereof, acid amido alkylation has been found to be possible, according to the invention, in the presence of sulphamic acid with a relatively high efficiency, in a number of cases even more than 60% calculated on glyoxylic acid. For the specific conversion of phenol, sulphamic acid and glyoxylic acid into (ortho and para)-hydroxyphenyl glycine, a conversion rate of more than 90% is reached. It has further been found, surprisingly, that if the reaction mixture contains water, sulphuric acid, which is e.g. formed during the reaction, can be separated off without a special process step being required for that purpose. Moreover, it has been found that the molar ratio of glyoxylic acid to phenol to sulphamic acid may be so chosen as to be virtually equimolar without having a significant adverse effect on the efficiency.

The compounds aimed at can be used as intermediates in the preparation of broad-spectrum antibiotics.

By applying the process according to the invention the product is generally obtained in a racemic form. Using processes known per se this product can subsequently be separated into the enantiomers.

As starting materials for the reaction with glyoxylic acid use can be made of aromatic compounds such as benzene—with or without substitution, for instance phenol —cycloalkenes or alkenes, for instance isobutene or cyclohexene. These compounds usually have 2-20 carbon atoms and may be substituted, for instance, with an hydroxy group or an alkyl or alkoxy group with 1-6 carbon atoms or a halogen. By applying the process according to the invention α-amino acids are obtained according to formula 1, where R represents an aryl group or a substituted aryl, cycloalkyl or alkyl group, in which process the substituents may, for instance, be an hydroxy or alkyl group, or a halogen.

In the process according to the invention the starting material used for the preparation of, for instance, p-hydroxyphenyl glycine may also be p-hydroxy mandelic acid according to formula (4)

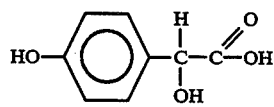

instead of phenol and glyoxylic acid.

Instead of glyoxylic acid it is also possible to use a precursor or a derivative of glyoxylic acid such as, for instance, a dihalo acetic acid, a glyoxylic acid (hemi)acetal, glyoxylic acid ester (hemi)acetal, a glyoxylic acid halide, glyoxylic acid ester or glyoxylic acid amide.

The molar ratio of sulphamic acid to glyoxylic acid to be applied in the process according to the invention is not critical and is usually between 1:2 and 2:1. Preference is given to the use of a virtually equimolar amount of sulphamic acid calculated on glyoxylic acid, for instance a molar ratio of between 0.9:1.1 and 1.1:0.9.

The molar ratio of aromatic compound or (cyclo)alkene to glyoxylic acid is not critical either and is usually between 1:2 and 2:1. Here again preference is given to the use of a virtually equimolar amount of aromatic compound or (cyclo)alkene calculated on glyoxylic acid, for instance a molar ratio of aromatic compound or (cyclo)alkene to glyoxylic acid of between 0.9:1.1 and 1.1:0.9.

The reaction is usually carried out in an aqueous medium, which may also contain an organic solvent.

Preferably a strong acid, for instance sulphuric acid, is added to the reaction mixture as well. The fact is that it has proved to be possible to reach higher efficiencies when the reaction medium also contains a catalytic amount of strong acid.

By applying the process according to the invention it is also quite possible without prior isolation to esterify the amino acid obtained as a reaction product. It has been found to be highly convenient if the esterification is carried out with an alcohol under the influence of a strong acid such as, for instance, sulphuric acid, oleum, benzene sulphonic acid and p-toluene sulphonic acid. The alcohol used in the esterification is mostly an aliphatic, monovalent alcohol with 1-4 carbon atoms. As customary in esterification processes, an excess of alcohol is used also in the process according to the invention, for instance 5-10 times as much alcohol as stoechiometrically required. The amount of concentrated acid in the esterification can be varied. To obtain a good result, strong acid is mostly used. In order to avoid hydrolysis of the ester it is to be recommended to keep the water content of the reaction mixture as low as possible. That is why preference is given to removing the water by continuous distillation before and/or during the esterification.

It is possible also for the resulting ester to be amidated without prior isolation, so that the corresponding amide becomes accessible. To this end, for instance, the reaction mixture is contacted, optionally under pressure, with ammonia.

According to a convenient mode of applying the process according to the invention, sulphamic acid, phenol, optionally sulphuric acid or an other strong acid and glyoxylic acid are successively added to water at room temperature for the preparation of p-hydroxyphenyl glycine, upon which the resulting suspension, while being stirred, is kept at a temperature of 20°–90° C. for 3–15 hours. The reaction mixture is subsequently neutralized with, for instance, ammonia to a pH of 2–6 at a temperature of 50°–100° C. again while being stirred After cooling to a temperature of 10°–50° C., the p-hydroxyphenyl glycine suspension formed is filtered and washed.

The suspension obtained can be converted without prior isolation into the corresponding methyl ester. To this end, for instance, methanol is added to the crude reaction mixture first, part of which methanol is subsequently distilled off again; then, once again, an amount of methanol and also sulphuric acid are added to the reaction mixture, upon which the reaction mixture is kept at a temperature of between 60° and 90° C. for 0.5 to 2 hours and the excess of methanol is partly removed by distillation. While being stirred and cooled, the reaction mixture is poured out into a mixture of water and ammonia. The methyl ester of p-hydroxyphenyl glycine formed is subsequently recovered after filtration and washing.

The methyl ester present in the reaction mixture can subsequently, again without prior isolation, be converted into the corresponding amide. To this end, for instance, the ester solution is added to ammonia and, while being stirred, kept at a temperature of 20°–50° C. for 10–25 hours. The slurry is then poured out into water. The amide is recovered after filtration and washing.

The invention will be further elucidated by means of the following examples without, however, being limited thereto.

EXAMPLE I

To 90 ml water were successively added, at room temperature, during stirred, 48.5 grammes (0.50 mole) sulphamic acid, 40.0 grammes (0.42 mole) phenol, 10 ml (0.18 mole) sulphuric acid and 58.7 grammes (0.40 mole) 50.4%-(wt) aqueous glyoxyl acid solution. While being stirred, the resulting suspension was kept at a temperature of 70° C. for 4 hours. After half an hour the colour of the solution was yellow. The reaction was faintly exothermic. Using 90 ml 25%-(wt) ammonia (1.20 moles) the reaction mixture was subsequently neutralized to pH=4–5 at a temperature of 60°–75° C. while being stirred. After cooling to a temperature of 25°–30° C., the resulting p-hydroxyphenyl glycine suspension, total volume 250 ml, was filtered over a glass filter and washed on the filter with successively 3×20 ml water and 3 ×20 ml methanol. The yield after drying was 41.0 grammes. Purity:>95% d,l-p-hydroxyphenyl glycine (HPLC). The efficiency based on glyoxylic acid is 61.4%.

EXAMPLE II

To a mixture of 85 ml H₂O, 107 grammes (1.1 moles) sulphamic acid and 94 grammes (1 mole) phenol was metered at 50° C. during stirring in 2 hours 148 grammes (1 mole) 50%-(wt) aqueous glyoxylic acid solution. The mixture was subsequently stirred for 4 hours at a temperature of 70° C. After that, using 25% (wt) ammonia, it was neutralized at 70° C. After cooling to a temperature of 25° to 30° C., the suspension was filtered. After washing with 3×60 ml H₂O and subsequent drying, 99 grammes dry product was obtained. The efficiency calculated on glyoxylic acid was 59.5%. Purity of solid:>97% d,l-p-hydroxyphenyl glycine (HPLC).

EXAMPLE III

To 90 ml water were successively added, at room temperature, during stirring, 78 grammes (0.8 mole) sulphamic acid, 40 grammes (0.42 mole) phenol and 58.7 grammes (0.40 mole) 50%-(wt) aqueous glyoxylic acid solution. While being stirred, the resulting suspension was kept at 97° C. for 3 hours. After cooling to 70° C., the suspension was neutralized to pH=4 using 25%-(wt) ammonia. After cooling to 20° C., the suspension was filtered and washed with 3×20 ml water. After drying, 34 grammes product was obtained.

Purity:>95% d,l-p-hydroxyphenyl glycine (HPLC).

EXAMPLE IV

To 300 ml water were successively added, at room temperature, during stirring, 282 grammes (3 moles) phenol and 320 grammes (3,3 moles) sulphamic acid. At 28° C. 457 grammes (3.08 moles) glyoxylic acid (50% wt) was metered in 8 hours. The mixture was subsequently stirred at 28° C. for 15 hours. After that, 1000 ml water was added and heated to 65° C. At 65° C. the suspension was subsequently stirred for 6 more hours. Using 25% (wt) ammonia the suspension was neutralized in 1.5 hours to pH=4.1, upon which it was cooled to 40° C. in 2 hours. At this temperature, it was stirred for 1 more hour and subsequently filtered, followed by washing with 3×150 ml water. After drying, 324 grammes product was obtained.

The efficiency calculated on glyoxylic acid was: 65%.

Purity:>98% d,l-p-hydroxyphenyl glycine (HPLC).

EXAMPLE V

To 300 ml water were successively added, at room temperature, during stirring, 282 grammes (3 moles) phenol and 450 grammes (4 6 moles) sulphamic acid At 30° C., 450 grammes (3 moles) glyoxylic acid was metered in 6 hours. The mixture was subsequently stirred for 15 hours at 28° C. After that, 1000 ml water was added and heated to 65° C. The suspension was subsequently stirred for two more hours at 65° C. In 1.5 hours it was neutralized to pH=4 at a temperature of 70° C. using 25% (wt) ammonia, upon which it was cooled to 40° C. At this temperature it was stirred for 1 more hour, upon which it was filtered, followed by washing with 3×150 ml water. After drying, 330 grammes product was obtained.

Purity:>98% d,l-p-hydroxyphenyl glycine (HPLC).

EXAMPLE VI

Preparation of the methyl ester of p-hydroxyphenyl glycine.

To 25 ml water were added, at room temperature, during stirring, 0.4 mole (40 grammes) phenol and 0.4 mole (40 grammes) sulphamic acid. After that, 0.4 mole (58.7 grammes) glyoxylic acid was metered for 20 minutes at 68°–71° C. This mixture was kept at a temperature of 70° C. for 1.5 hours.

Subsequently, 70 ml toluene was added and water was removed azeotropically at a temperature of 92°–100° C. for 1 hour. After addition of 70 ml methanol the mixture was kept at 74° C. for 2 hours, upon which phase separation took place at 25° C. The methanolic solution was poured out into a mixture of 100 ml water and 60 ml 25%-(wt) ammonia (20 minutes; 20°–40° C.). The ester formed was filtered off at 25° C. and washed on a glass filter with successively 3×25 ml water and 3×25 ml methanol. The wet weight was 64.6 grammes; the dry weight was 42.9 grammes.

The efficiency was 59.6%.

EXAMPLE VII

Preparation of the Methyl Ester of P-Hydroxyphenyl Glycine

To 25 ml water were added, at room temperature, during stirring, 0.4 mole (40 grammes) phenol and 0.4 mole (40 grammes) sulphamic acid. After that, 0.4 mole (58.7 grammes of a 50.2%-(wt) solution of) glyoxylic acid was metered at 68°–70° C. for 45 minutes. This mixture was kept at a temperature of 70° C. for 2 hours.

Subsequently, 100 ml toluene was added and 52 ml water was removed azeotropically at a temperature of 92°–111° C. for 75 minutes. After addition of 100 ml methanol and 10 ml concentrated sulphuric acid, the mixture was kept at 76° C. for 2.5 hours, upon which phase separation took place at 20° C. The methanolic solution was added in drops to a mixture of 175 ml water and 75 ml concentrated ammonia during cooling. The ester formed was filtered off at 20° C. and washed on a glass filter using successively 3×25 ml water and 3×25 ml methanol. The wet weight was 62.8 grammes; the dry weight was 4 5.8 grammes.

The efficiency was 63.6%.

EXAMPLE VIII

Preparation of P-Hydroxyphenyl Glycine Amide

To 75 ml water were added, at room temperature, during stirring, 1.0 mole (100 grammes) phenol and 1.0 mole (100 grammes) sulphamic acid. Subsequently, 1.0 mole (146.8 grammes of a 50.2%-(wt) solution of) glyoxylic acid was metered at 69°–71° C. for 30 minutes. This mixture was kept at a temperature of 70° C. for 1.5 hours.

Subsequently, 250 ml toluene was added and 145 ml water was removed azeotropically at a temperature of 92°–100° C. for 1.5 hours. After addition of 200 ml methanol and 25 ml concentrated sulphuric acid, the mixture was kept at 77° C. for 2 hours, upon which phase separation took place at 30° C. The methanolic solution was metered to 250 ml 25%-(wt) ammonia and kept at 30° C. for 16 hours at an NH$_3$ pressure of 1.5 bar. After relieving the NH$_3$ pressure, the suspension was poured out into 250 ml water. The amide formed was filtered off and washed on a glass filter with successively 3×50 ml water and 3×50 ml methanol. The wet weight was 85 grammes; the dry weight was 70.6 grammes. The p-hydroxyphenyl glycine amide was tlc-pure and free from sulphate. HPLC measurements revealed that the content of o-hydroxyphenyl glycine amide was lower than 0.1%.

The efficiency was 42.5%.

EXAMPLE IX

Preparation of P-Hydroxyphenyl Glycine Starting From P-Hydroxy Mandelic Acid and Sulphamic Acid To 70 ml water were added, at room temperature, during stirring, 0.4 mole (84 grammes) sodium salt of p-hydroxy mandelic acid and 0.4 mole (38.8 grammes) sulphamic acid. This mixture was kept at a temperature of 105° C. for 7 hours. At a temperature of 70°–90° C., the reaction mixture was subsequently neutralized to an acidity of pH=5 using 32 ml 25%-(wt) ammonia After cooling to 30° C., the crystalline p-hydroxyphenyl glycine was isolated by means of filtration and washed on the filter with successively 3×20 ml water and 3×25 ml methanol. The wet weight was 53.5 grammes; the dry weight was 45.8 grammes.

The efficiency was 68.8%.

Purity:>99% d,l-p-hydroxyphenyl glycine (HPLC).

EXAMPLE X

Preparation of the Methyl Ester of P-Hydroxyphenyl Glycine

To a mixture of 15 grammes water, 0.8 mole (80 grammes) phenol and 0.8 mole (80 grammes) sulphamic acid were metered at a temperature of 65°–70° C. under stirring for 20 minutes 0.8 mol (96 grammes) glyoxylic acid methylester hemiacetal. After stirring at 70° C. for 1 hour 2.5 moles (80 grammes) methanol were added. The mixture was kept another hour under stirring at 70° C. After cooling to 30° C. the reaction mixture was added to a mixture of 200 ml water and 200 ml 25% (wt) ammonia. The thus obtained suspension of methylester of p-hydroxyphenylglycine was filtered off at 30° C. and washed on a glass filter with successively 3×50 ml water and 3×50 ml methanol. The wet weight was 55 grammes; the dry weight of tlc-pure p-hydroxyphenylglycine was 48.0 grammes.

The efficiency was 33.1%.

EXAMPLE XI

Preparation of the Methyl Ester of P-Hydroxyphenyl Glycine

To a mixture of 30 grammes water, 0.8 mole (80 grammes) phenol and 0.8 mole (80 grammes) sulphamic acid were metered at a temperature of 65°–70° C. under stirring for 1 hour 0.8 mol (96 grammes) glyoxylic acid methylester hemiacetal. After stirring at 70° C. for 1 hour 5 moles (160 grammes) methanol were added. The mixture was kept another hour under stirring at 70° C. After cooling to 30° C. the reaction mixture was added to a mixture of 200 ml water and 200 ml 25% (wt) ammonia. The thus obtained suspension of methylester of p-hydroxyphenylglycine was filtered off at 30° C. and washed on a glass filter with successively 3×50 ml water and 3×50 ml methanol. The dry weight of tlc-pure p-hydroxyphenylglycine was 49.3 grammes.

The efficiency was 34%.

We claim:

1. Process for preparing an α-amino acid having the general formula (1):

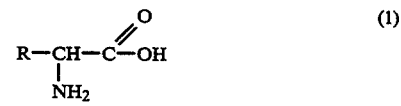

wherein R represents aryl, substituted aryl, cycloalkyl, substituted cycloalkyl, alkyl, or substituted alkyl in which process glyoxylic acid with the formula (2):

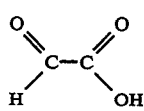 (2)

or a precursor or derivative thereof is contacted with at least one unsaturated compound selected from the group consisting of aromatic compounds, cycloalkenes and alkenes, in the presence of a N-containing compound, wherein sulphamic acid is used as the N-containing compound.

2. Process according to claim 1, wherein phenol is used as the unsaturated compound.

3. Process according to claim 1, wherein the molar ratio of sulphamic acid to glyoxylic acid is between 1.1:0.9 and 0.9:1.1.

4. Process according to claim 1, wherein the molar ratio of the at least one unsaturated compound to glyoxylic acid is between 0.9:1.1 and 1.1:0.9.

5. Process according to claim 1, wherein the reaction mixture also contains a strong acid.

6. Process for preparing an amino acid ester having the general formula (5):

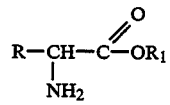 (5)

wherein R represents aryl, substituted aryl, cycloalkyl, or alkyl and $R_1$ represents the hydrocarbon residue of an alcohol, which comprises contacting a corresponding acid obtained according to claim 1 with an alcohol.

7. Process for preparing an amino acid amide having the general formula of:

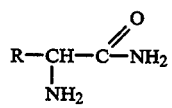

wherein said formula R represents an aryl group or a substituted aryl, cycloalkyl or alkyl group which comprises contacting an amino acid according to claim 1 with an alcohol whereby an ester is obtained, ammoniacally treating the thus obtained ester whereby an amino acid amide is obtained.

8. Process according to claim 6 wherein said $R_1$ is the residue of a aliphatic monovalent alcohol.

9. Process according to claim 8, wherein $R_1$ is the residue of a $C_1$ to $C_4$ aliphatic monovalent alcohol.

* * * * *